United States Patent
Fukuju et al.

(10) Patent No.: US 8,304,589 B2
(45) Date of Patent: *Nov. 6, 2012

(54) PROCESS OF MAKING A CHLORINATED HYDROCARBON

(75) Inventors: Tadahiro Fukuju, Shunan (JP); Kikuo Yamamoto, Shunan (JP); Masayuki Moriwaki, Shunan (JP); Yasutaka Komatsu, Shunan (JP); Akihiro Saito, Shunan (JP); Shunsuke Hosaka, Shunan (JP); Dai Tsunoda, Shunan (JP); Jun Kawakami, Shunan (JP)

(73) Assignee: Tokuyama Corporation, Shunan-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/406,238

(22) Filed: Feb. 27, 2012

(65) Prior Publication Data

US 2012/0157723 A1   Jun. 21, 2012

Related U.S. Application Data

(62) Division of application No. 13/319,912, filed as application No. PCT/JP2010/060695 on Jun. 17, 2010.

(30) Foreign Application Priority Data

| Jun. 24, 2009 | (JP) | 2009-150096 |
| Jul. 10, 2009 | (JP) | 2009-164149 |
| Sep. 9, 2009 | (JP) | 2009-208370 |
| Sep. 11, 2009 | (JP) | 2009-210812 |

(51) Int. Cl.
   *C07C 17/00*   (2006.01)

(52) U.S. Cl. .................. 570/247; 570/246; 570/257

(58) Field of Classification Search .................. None
See application file for complete search history.

(56) References Cited

U.S. PATENT DOCUMENTS

| 3,823,195 A |   | 7/1974 | Smith |   |
| 3,926,758 A |   | 12/1975 | Smith |   |
| 4,650,914 A | * | 3/1987 | Woodard | ............ 570/236 |
| 5,446,217 A |   | 8/1995 | Van Der Puy et al. |   |

FOREIGN PATENT DOCUMENTS

| JP | 50-4006 A | 1/1975 |
| JP | 60-36429 A | 2/1985 |
| JP | 2-47969 B2 | 10/1990 |
| JP | 2007-23050 A | 2/2007 |

OTHER PUBLICATIONS

International Search Report for International Patent Application No. PCT/JP2010/060695, mailed on Aug. 31, 2010.

* cited by examiner

*Primary Examiner* — Sudhakar Katakam

(74) *Attorney, Agent, or Firm* — Birch, Stewart, Kolasch & Birch, LLP

(57) ABSTRACT

A process of making a chlorinated hydrocarbon through a thermal dehydrochlorination step in which an unsaturated compound represented by the following general formula (2) is obtained by thermally decomposing a saturated compound represented by the following general formula (1).

$$CCl_3\text{—}CCl_{2-m}H_m\text{—}CCl_{3-n}H_n \quad (1)$$

$$CCl_2\text{=}CCl_{2-m}H_{m-1}\text{—}CCl_{3-n}H_n \quad (2)$$

(in the above formulas, m is 1 or 2, and n is an integer of 0 to 3.).

12 Claims, No Drawings

PROCESS OF MAKING A CHLORINATED HYDROCARBON

This application is a Divisional Application of copending U.S. patent application Ser. No. 13/319,912, filed Nov. 10, 2011, which is the U.S. National Phase of PCT/JP2010/060695, filed Jun. 17, 2010. Priority is claimed under 35 U.S.C. §120. This application also claims priority under 35 U.S.C. §119 to Japanese patent application nos. 2009-150096, filed in Japan on Jun. 24, 2001, 2009-164149, filed in Japan on Jul. 10, 2009, 2009-208370 filed in Japan on Sep. 9, 2009 and 2009-210812 filed in Japan on Sep. 11, 2009. The entire contents of all are herein incorporated by reference.

TECHNICAL FIELD

The present invention relates to a process of making a chlorinated hydrocarbon. More specifically, it relates to a process of making a high-purity chlorinated hydrocarbon by a simple method.

BACKGROUND ART

Chlorinated hydrocarbons are important as feedstocks or intermediates for the manufacture of various products such as agricultural chemicals, medicinal chemicals and freon alternate materials. For example, trichloroallyl diisopropylthiocarbamate which is useful as a herbicide can be manufactured from 1,1,1,2,3-pentachloropropane through 1,1,2,3-tetrachloropropene. The chlorinated hydrocarbons which are feedstocks or intermediates for agricultural and medicinal chemicals must have extremely high purity.

As the process of making such chlorinated hydrocarbons, there is known a three-stage reaction consisting of a first reaction for obtaining a chlorinated saturated hydrocarbon having 3 carbon atoms by adding carbon tetrachloride to an unsaturated compound having 2 carbon atoms, a second reaction for obtaining a chlorinated unsaturated hydrocarbon having 3 carbon atoms by dehydrochlorinating the chlorinated saturated hydrocarbon, and a third reaction for obtaining a chlorinated saturated hydrocarbon having 3 carbon atoms by further adding chlorine to the chlorinated unsaturated hydrocarbon. For example, JP-B 2-47969 discloses a process comprising the steps of carrying out an addition reaction between ethylene and carbon tetrachloride in the presence of a phase transfer catalyst comprising metallic iron and a phosphoryl compound to obtain 1,1,1,3-tetrachloropropane (first reaction), treating this in a sodium hydroxide aqueous solution in the presence of a quaternary ammonium salt or a quaternary phosphonium salt at a temperature of 40 to 80° C. to dehydrochlorinate it so as to obtain a trichloropropene mixture of 1,1,3-trichloropropene and 3,3,3-trichloropropene (second reaction), and applying ultraviolet light to the trichloropropene mixture in the presence of chlorine to chlorinate it so as to obtain 1,1,1,2,3-pentachloropropane (third reaction).

A person skilled in the art can obtain a chlorinated saturated or unsaturated hydrocarbon having desired numbers of carbon atoms and chlorine atoms by selecting an appropriate feedstock compound and carrying out part or all of the above three-stage reaction.

However, the above prior art process of making a chlorinated hydrocarbon has the following problems to be solved in each stage.

In the first reaction, although the iron-phosphoryl compound catalyst in use shows high reactivity right after it is prepared, its activity sharply drops with the passage of time. Therefore, to obtain a desired high degree of conversion, a large amount of the catalyst must be used. However, when a large amount of the catalyst is used, it is difficult to control the reaction due to a sharp rise in reactivity in the initial stage of the reaction, whereby the reaction yield of an object of interest may be impaired. Also when a large amount of the catalyst is used, it takes lots of labor and cost to dispose of the waste catalyst, thereby impeding the curtailment of production cost. Further, the surface of the metallic iron used in the preparation of the iron-phosphoryl compound catalyst is gradually oxidized during its storage, and the initial reaction rate is greatly changed by its oxidized state.

In the second reaction, there is a problem with the cost of sodium hydroxide which is consumed in considerable quantity, and also it takes a lot of labor to dispose of the organic chlorine compound which is dissolved in a water phase to be discarded.

In the optical chlorination reaction which is the third reaction, the reaction time (residence time) must be prolonged to achieve a sufficiently high degree of reaction conversion.

Further, to obtain 1,1,1,2,3-pentachloropropane having high purity as a chlorinated hydrocarbon, the distillation purification of the obtained product is generally carried out after the third reaction. However, when this chlorinated hydrocarbon having a large number of chlorine atoms is purified by distillation, it is very difficult to separate impurities from the chlorinated hydrocarbon. Therefore, an extremely high-performance distillation column is required to obtain a high-purity product, and it takes a long time to carry out precision distillation, thereby causing a cost problem.

As described above, in the three-stage reaction for the manufacture of a chlorinated hydrocarbon, it is desired that an addition reaction should be carried out efficiently at a stable reaction rate to obtain an object of interest at a high degree of conversion while the amount of the catalyst is reduced in the first reaction; a dehydrochlorination reaction should be carried out in such a manner that the production of a by-product to be disposed of is suppressed without using an expensive alkali source in the second reaction; and a chlorination reaction having higher efficiency should be carried out in the third reaction.

DISCLOSURE OF THE INVENTION

The present invention which has been made to improve the above situation is aimed to provide a process of making a chlorinated hydrocarbon efficiently by simple operation.

According to the present invention, the above object is attained by a process of making a chlorinated hydrocarbon through a thermal dehydrochlorination step in which a saturated compound represented by the following general formula (1) is thermally decomposed to obtain an unsaturated compound represented by the following general formula (2). After this dehydrochlorination step, a chlorination step in which the unsaturated compound represented by the following general formula (2) is reacted with chlorine to obtain a saturated compound represented by the following general formula (3) can be further carried out.

$$CCl_3-CCl_{2-m}H_m-CCl_{3-n}H_n \quad (1)$$

$$CCl_2=CCl_{2-m}H_{m-1}-CCl_{3-n}H_n \quad (2)$$

$$CCl_3-CCl_{3-m}H_{m-1}-CCl_{3-n}H_n \quad (3)$$

(in the above formulas, m is 1 or 2, and n is an integer of 0 to 3.)

The saturated compound represented by the above general formula (1) is preferably a saturated compound represented by the following general formula (1') which is obtained by an addition reaction step in which carbon tetrachloride is added to an unsaturated compound represented by the following general formula (0) in a liquid-phase reaction system in the presence of an iron-phosphate catalyst.

$$CCl_{2-m}H_m = CCl_{2-p}H_p \qquad (0)$$

$$CCl_3 - CCl_{2-m}H_m - CCl_{3-p}H_p \qquad (1')$$

(in the above formulas, m is 1 or 2, and p is an integer of 0 to 2, with the proviso that m≧p.)

A detailed description is subsequently given of the present invention in each stage of the reaction.

<First Reaction>

The first reaction in the present invention is an addition reaction for obtaining a saturated compound represented by the above general formula (1') through an addition reaction between carbon tetrachloride and an unsaturated compound represented by the above general formula (0). This reaction is preferably carried out in a liquid-phase reaction system in the presence of a catalyst.

Examples of the unsaturated compound represented by the above general formula (0) include ethylene, vinyl chloride, 1,1-dichloroethylene, 1,2-dichloroethylene and 1,1,2-trichloroethylene. Out of these, ethylene or vinyl chloride is preferably used.

The type of the chloropropane which is a saturated compound represented by the above general formula (1') obtained by this reaction depends on the type of the unsaturated compound represented by the above general formula (0) used as a feedstock. For example, when ethylene is used as a feedstock, 1,1,1,3-tetrachloropropane is obtained as the saturated compound represented by the above general formula (1'). When vinyl chloride is used as a feedstock, 1,1,1,3,3-pentachloropropane is obtained as the saturated compound represented by the above general formula (1'). It is obvious for a person having ordinary skill in the art what product is obtained as the saturated compound represented by the above general formula (1') when another compound is used as the unsaturated compound represented by the above general formula (0).

Examples of the catalyst in use include iron-phosphate catalysts, iron-aprotic polar solvent catalysts and copper-amine catalysts. Out of these, iron-phosphate catalysts are preferred.

This reaction is carried out while an iron-phosphate catalyst is existent in a liquid phase. This iron-phosphate catalyst is prepared by bringing a predetermined amount of iron and a predetermined amount of a phosphate into contact with each other in a liquid-phase reaction system (that is, in liquid carbon tetrachloride). Contact between iron and the phosphate may be carried out by injecting the whole amounts of iron and the phosphate into the reaction system before the start of the reaction, or by adding the whole amount of iron and part of the phosphate before the start of the reaction and further adding the remaining phosphate during the proceeding of the addition reaction. The expression "before the start of the reaction" means a point of time before the unsaturated compound represented by the above general formula (0) is introduced into carbon tetrachloride.

Examples of the iron used herein include metallic iron, pure iron, soft iron, carbon steel, ferrosilicon steel and alloys containing iron (such as stainless steel). Any shape of the iron may be powdery, granular, massive, rod-like, spherical, lamellar or fibrous, and the iron may be a metal piece which is obtained by carrying out the arbitrary processing of any one of these, or distilled filler. Examples of the above processed metal piece include coils, nets, steel wool and other amorphous pieces; and examples of the above distilled filler include Raschig ring and helix. Although the iron may be in any one of these forms, it is preferably powdery or fibrous in order to ensure a sufficient contact area with the phosphate and the reactants. From the same point of view, the specific surface area of the iron measured by the BET method using nitrogen as an adsorbate is preferably 0.001 to 5 $m^2/g$.

When the whole amount of the phosphate is added before the start of the reaction, the amount of the iron is preferably not less than 0.001 mole, more preferably not less than 0.005 mole, much more preferably not less than 0.01 mole, particularly preferably not less than 0.05 mole based on 1 mole of carbon tetrachloride in use to obtain a high degree of reaction conversion and high selectivity at the same time. The upper limit of the amount of the iron is not particularly limited. Even when the amount of the iron is increased, it rarely has an effect on activity and selectivity. However, the amount of the iron which is wasted without being used in the reaction increases, which is economically disadvantageous. From this point of view, the amount of the iron is preferably not more than 10 moles, more preferably not more than 5 moles, much more preferably not more than 1 mole, particularly preferably not more than 0.1 mole based on 1 mole of carbon tetrachloride in use.

The above phosphate is, for example, a compound represented by the following general formula (4).

(4)

(in the above formula (4), $R^1$ is a phenyl group or alkyl group having 1 to 4 carbon atoms, and $R^2$ and $R^3$ are each independently a hydrogen atom, phenyl group or alkyl group having 1 to 4 carbon atoms.)

Examples of the phosphate include trimethyl phosphate, triethyl phosphate, tripropyl phosphate, tributyl phosphate, diethyl phosphate, dibutyl phosphate, monophenyl phosphate, monobutyl phosphate, dimethylphenyl phosphate, diethylphenyl phosphate, dimethylethyl phosphate and phenylethylmethyl phosphate. Out of these, trialkyl phosphates of the above general formula (4) in which $R^1$, $R^2$ and $R^3$ are all alkyl groups having 1 to 4 carbon atoms are preferred, and trimethyl phosphate, triethyl phosphate, tripropyl phosphate and tributyl phosphate are particularly preferred.

The amount of the phosphate is preferably not less than 0.001 mole, particularly preferably not less than 0.002 mole based on 1 mole of carbon tetrachloride in use in order to ensure a high degree of conversion and high selectivity. Although the upper limit of the amount of the phosphate is not particularly limited, when the amount is made too large, the amount of the phosphate which is wasted without being used in the reaction increases, which is economically disadvantageous. From this point of view, the amount of the phosphate is preferably not more than 5 moles, more preferably not more than 1 mole and may be not more than 0.5 mole based on 1 mole of carbon tetrachloride.

The reaction temperature of the first reaction is preferably 70 to 180° C., more preferably 90 to 150° C. in order to obtain a high degree of conversion and high selectivity at the same time. The reaction pressure may be a pressure at which the reaction system can maintain a liquid phase at the above reaction temperature, generally 0.05 to 3 MPaG, preferably 0.1 to 2 MPaG. When the reaction pressure is lower than 0.05

MPa, the content of the feedstock (the unsaturated compound represented by the above general formula (0)) in the liquid phase becomes too low, whereby the reaction additive rate may become insufficient. When the reaction pressure is higher than 3 MPa, the production rate of a multimer becomes high, whereby selectivity may be impaired disadvantageously.

The reaction time of the first reaction is preferably 2 to 24 hours, more preferably 2 to 10 hours. When the reaction time is shorter than 2 hours, the degree of reaction conversion may become unsatisfactory and when the reaction time is longer than 24 hours, the reaction is impractical.

In the present invention, in the above first reaction, it is preferred that the whole amount of the iron and part of the phosphate should be added before the start of the reaction and the remaining phosphate should be added during the proceeding of an addition reaction because the controllability of the reaction is improved, selectivity is increased, and the amount of the iron in use can be reduced.

The amount of the iron which is entirely added before the start of the reaction can be made smaller than the above value which is specified as the lower limit of the amount of the iron when the whole amount of the phosphate is added before the start of the reaction. In this case, the amount of the iron is preferably not less than 0.0001 mole, more preferably not less than 0.0005 mole, much more preferably not less than 0.001 mole, particularly preferably not less than 0.005 mole based on 1 mole of carbon tetrachloride in use. The upper limit of the amount of the iron is set from the economical point of view. In this case, the amount of the iron is preferably not more than 1 mole, more preferably not more than 0.5 mole, much more preferably not more than 0.1 mole based on 1 mole of carbon tetrachloride in use.

In this reaction, it is preferred that part of the phosphate should be added before the start of the reaction and the remaining phosphate should be added during the proceeding of the addition reaction. The addition of the remaining phosphate may be carried out only once, several times in fractional amounts, or continuously. When the remaining phosphate is added several times in fractional amounts, the number of times of addition is preferably 2 to 10, more preferably 2 to 6.

The total amount of the phosphate (the total of the amount of the phosphate to be added before the start of the reaction and the amount of the remaining phosphate) is preferably not less than 0.001 mole, particularly preferably not less than 0.002 mole based on 1 mole of carbon tetrachloride in use. The total amount of the phosphate when it is added in fractional amounts is not particularly limited. However, when the total amount of the phosphate is made too large, the amount of the phosphate which is wasted without being used in the reaction becomes large as well, which is economically disadvantageous. From this point of view, the total amount of the phosphate when it is added in fractional amounts is preferably not more than 5 moles, more preferably not more than 1 mole and may be not more than 0.5 mole based on 1 mole of carbon tetrachloride.

The process in which the phosphate is added in fractional amounts has an advantage that, even when the amount of the phosphate is made smaller than that of the prior art, for example, the process disclosed by the above JP-B 2-47969, a compound of interest can be produced efficiently at a higher degree of conversion and a stable reaction rate.

In a preferred example of the reaction, part of the phosphate is added before the start of the reaction. The amount of the phosphate to be added before the start of the reaction is preferably not less than 0.0005 mole, more preferably not less than 0.001 mole based on 1 mole of carbon tetrachloride in use. The upper limit of the amount of the phosphate to be added before the start of the reaction is preferably not more than 80%, more preferably not more than 70% of the total amount of the phosphate regardless of the addition manner of the remaining phosphate (whether it is added only once, several times in fractional amounts or continuously) or regardless of the number of times of addition when the remaining phosphate is added several times in fractional amounts. By setting the amount of the phosphate to be added before the start of the reaction to the above range, the reaction can be started stably and it is easy to control the reaction with the result that a high degree of conversion can be achieved.

The addition reaction which has been thus started is preferably carried out while the consumption speed of the unsaturated compound represented by the above general formula (0) is continuously monitored. The continuous monitoring of the consumption speed of the unsaturated compound can be carried out any time by comparing the amount of the unsaturated compound supplied continuously in a gaseous state with the amount of the unsaturated compound discharged from a gas phase to maintain an appropriate reaction pressure in the liquid-phase batch reaction under the circulation of the gas phase. When the consumption speed drops to a predetermined value from the initial value, the addition of the remaining phosphate is carried out or started.

When the remaining phosphate is added only once and the consumption speed of the unsaturated compound becomes preferably 5 to 50%, more preferably 10 to 40% of the average consumption speed for 60 minutes from the start of the reaction, the whole amount of the remaining phosphate is added. The consumption speed of the unsaturated compound which has dropped once is recovered by this addition, and the residual addition reaction proceeds while the consumption speed gradually drops again after that.

When the remaining phosphate is added several times in fractional amounts and the consumption speed becomes preferably 5 to 50%, more preferably 10 to 40% of the average consumption speed for 60 minutes from the start of the reaction, first time of addition of the phosphate is carried out. The consumption speed of the unsaturated compound which has dropped once is recovered by this first time of addition and gradually drops again after that. When the consumption speed of the unsaturated compound becomes preferably 5 to 50%, more preferably 10 to 40% of the average consumption speed for 60 minutes from the start of the reaction again, second time of addition of the phosphate is carried out. The consumption speed of the unsaturated compound is recovered again by this addition. Thereafter, the phosphate can be added a predetermined number of times in fractional amounts by monitoring the consumption speed of the unsaturated compound represented by the above general formula (0) continuously.

Preferably, the fractional amount of the remaining phosphate to be added each time when it is added several times in fractional amounts is set to the same value or gradually reduced each time.

When the remaining phosphate is added continuously and the consumption speed becomes preferably 5 to 50%, more preferably 10 to 40% of the average consumption speed for 60 minutes from the start of the reaction, the addition of the remaining phosphate is started. The whole amount of the remaining phosphate is added continuously over preferably 1 to 400 minutes, more preferably 2 to 360 minutes from the above point of time.

The remaining phosphate is preferably added only once or continuously. When the remaining phosphate is added only once, the operation becomes easy and when the remaining phosphate is added continuously, it is easy to control the reaction.

The total reaction time of the addition reaction which is carried out as described above is preferably 2 to 12 hours, more preferably 2 to 10 hours.

The reaction mixture obtained as described above contains an object of interest which has been converted at a high degree of conversion and high selectivity. Therefore, when unreacted carbon tetrachloride (its content is very low), the iron-phosphate catalyst residue and an excess of the unsaturated compound represented by the above general formula (0) contained in the reaction mixture obtained by the method for adding the remaining phosphate are separated from the reaction mixture, the reaction mixture can be used as a product as it is in many cases or can be supplied into the reaction of the subsequent step as it is. Although purification can be optionally carried out after the first reaction, the purification method may be simple, for example, simple purification having 2 to 10 theoretical stages can provide a high-purity product.

<Second Reaction>

The second reaction in the present invention is a thermal dehydrochlorination step in which an unsaturated compound represented by the above general formula (2) is obtained by thermally decomposing a saturated compound represented by the above general formula (1).

The inventors of the present invention have found that the saturated compound represented by the above general formula (1) readily causes a dehydrochlorination reaction by heating. This characteristic feature is assumed to be due to the $CCl_3$ group contained in the saturated compound represented by the above general formula (1). That is, the inventors of the present invention have found that Cl contained in the above $CCl_3$ group is readily desorbed by heat, thereby making it possible to cause a dehydrochlorination reaction by thermal decomposition easily at a short heating time of 1 to 10 seconds. As a result, an extremely easy second reaction has been realized.

When a dehydrochlorination reaction is to be carried out by the thermal decomposition of a chlorinated saturated hydrocarbon having no $CCl_3$ group other than the saturated compound represented by the above general formula (1), along residence time is required with the result that the amount of a by-product produced during the reaction increases and carbon formed by excessive thermal decomposition separates out into a pipe.

Examples of the saturated compound represented by the above formula (1) include 1,1,1-trichloropropane, 1,1,1,2-tetrachloropropane, 1,1,1,3-tetrachloropropane, 1,1,1,2,3-heptachloropropane, 1,1,1,3,3-pentachloropropane, 1,1,1,2,3,3-hexachloropropane, 1,1,1,3,3,3-hexachloropropane and 1,1,1,2,3,3,3-heptachloropropane. When 1,1,1,3-tetrachloropropane is used out of these, 1,1,3-trichloropropene which is useful as an intermediate for various compounds is obtained as the unsaturated compound represented by the above general formula (2) by the second reaction advantageously.

The saturated compound represented by the above general formula (1) used herein is preferably a saturated compound represented by the above general formula (1') which is produced by the above first reaction.

Examples of the unsaturated compound represented by the above general formula (2) which is obtained by the second reaction include 1,1-dichloropropene, 1,1,2-trichloropropene, 1,1,3-trichloropropene, 1,1,2,3-tetrachloropropene, 1,1,3,3-tetrachloropropene, 1,1,2,3,3-pentachloropropene, 1,1,3,3,3-pentachloropropene and 1,1,2,3,3,3-hexachloropropene which are enumerated in the order of the above compounds listed as examples of the saturated compound represented by the above formula (1).

The second reaction in the present invention can be carried out by heating the saturated compound represented by the above general formula (1) at a temperature equal to or higher than the thermal decomposition temperature of the compound.

This thermal decomposition reaction is preferably carried out in a gas phase, and its reaction system may be either circular or batch. However, since the thermal decomposition reaction of the second reaction in the present invention can achieve a high degree of reaction conversion in a short reaction time, the circulation system is preferred from the viewpoint of reaction efficiency.

The above heating temperature is preferably 300 to 600° C., more preferably 350 to 550° C. The heating time (residence time) is preferably 1 to 10 seconds, more preferably 1 to 5 seconds, much more preferably 1 to 3 seconds. When the heating temperature is lower than 300° C. or the heating time is shorter than 1 second, thermal decomposition becomes difficult and when the heating temperature is higher than 600° C. or the heating time is longer than 10 seconds, the reaction selectivity may lower disadvantageously.

Heating in the second reaction of the present invention may be carried out by a known method. The reactor is preferably a reaction tube (decomposition furnace) having a heater on the outer wall. Examples of the material of the reactor include quartz, ceramics and metals. As the heater may be used a burner, an electric heater or a high-frequency heater.

In the second reaction, to supply the saturated compound represented by the above formula (1) into the reactor, the compound is gasified by a carburetor and introduced into the reactor as a gas, or the liquid compound is sprayed to be introduced into the reactor. At this point, only the saturated compound represented by the above formula (1) may be supplied into the reactor, or a mixture of the saturated compound represented by the above formula (1) and a suitable diluent gas may be introduced into the reactor. As the diluent gas used herein is preferably used an inert gas such as nitrogen, argon or helium, out of which nitrogen is preferred from the viewpoint of cost required for the diluent gas. It is preferred to adjust the oxygen content of the diluent gas to not more than 1 wt %. When the product obtained by the dehydrochlorination step of the second reaction contains water, an extra purification step is required to remove water, which is economically disadvantageous. To avoid this, the water content of the diluent gas is preferably adjusted to not more than 1,000 ppm by weight.

Although it is possible to suppress the occurrence of a drastic reaction by diluting the saturated compound represented by the above formula (1), when the saturated compound is diluted too much, the reaction efficiency degrades. To achieve a good balance between them, the dilution factor of the saturated compound is preferably 1.1 to 2 times.

The reaction pressure in the second reaction is not particularly limited, and the second reaction can be carried out under reduced pressure or increased pressure. When the second reaction is carried out under increased pressure, the reactor can be made small in size. However, as the reaction pressure becomes higher, the precipitation of carbon in a pipe tends to occur more often. Since it is possible to carry out dehydrochlorination by thermal decomposition very efficiently when the second reaction is carried out at normal pressure in the present invention, the selection of the reaction under increased pressure is almost impractical.

Although thermal decomposition in the second reaction proceeds sufficiently quickly without a catalyst, it may be carried out by heating in the presence of a catalyst by installing a fixed bed or fluid bed type catalyst bed in the above reactor. Thereby, a high degree of conversion can be achieved even at a relatively low temperature out of the above preferred temperature range advantageously. Examples of the catalyst used herein include oxides such as silica, alumina and titania, and activated carbon.

It is preferred from the viewpoint of reducing the amount of the by-product that the gas after the second reaction should be cooled swiftly. It is advantageous that the gas discharged from the thermal decomposition reactor at the above thermal decomposition temperature should be cooled to a temperature preferably lower than 300° C., more preferably lower than 200° C., particularly preferably lower than 100° C. within preferably 2 seconds. This cooling may be carried out by a known method, for example, a heat exchange method with a supply gas or a method of cooling with the latent heat of vaporization by spraying droplets of a dehydrochlorinated product.

The reaction mixture of the second reaction (exhaust gas from the reactor) obtained as described above may be used in the third reaction as it is or after hydrogen chloride produced (by-produced) by the second reaction is removed by some means (for example, distillation). It is one of the features of the process of the present invention that hydrogen chloride (HCl) does not need to be removed from the exhaust gas which is the reaction mixture. Thereby, an apparatus for separating hydrogen chloride, such as a distillation column or an intermediate tank, does not need to be installed between the reactor for a dehydrochlorination reaction and the reactor for a chlorination reaction, thereby making it possible to design a compact apparatus for the manufacture of a chlorinated hydrocarbon.

The expression "the reaction mixture (exhaust gas) may be used in the third reaction as it is" means that the exhaust gas from the reactor for the second reaction is transferred to a reactor for the third reaction without any special purification (removal of hydrogen chloride in particular) while it still has composition at the exist and does not exclude the adjustment of the gas temperature after discharge and the addition of a chlorine gas required for the third reaction.

<Third Reaction>

The third reaction in the present invention is a chlorination step in which a saturated compound represented by the above general formula (3) is obtained by reacting the unsaturated compound represented by the above general formula (2) with chlorine. This third reaction proceeds swiftly simply by bringing the unsaturated compound represented by the above general formula (2) into contact with chlorine.

Specific examples of the saturated compound represented by the above general formula (3) include 1,1,1,2,3-pentachloropropane, 1,1,1,2,3,3-hexachloropropane, 1,1,1,2,3,3,3-heptachloropropane, 1,1,1,2,2,3,3-heptachloropropane and 1,1,1,2,2,3,3,3-octachloropropane. Out of these, 1,1,1,2,3-tetrachloropropane is useful as an intermediate for various compounds and preferred. It would be obvious for a person having ordinary skill in the art what product is obtained as the saturated compound represented by the above general formula (3) according to the unsaturated compound represented by the above general formula (2) in use.

The following advantages can be obtained by carrying out the third reaction of the present invention after the above second reaction.

The first advantage is that the product of the second reaction in the present invention rarely contains water. In the present invention, since the dehydrochlorination step which is the above second reaction is carried out preferably by a thermal decomposition reaction in a gas phase, the exhaust gas of the second reaction rarely contains water. Therefore, a large-scale dehydration apparatus is not required before or after the third reaction.

The second advantage is that the product of the second reaction rarely contains iron. In general, it is preferred that iron should not be existent in the step for chlorinating the chlorinated unsaturated hydrocarbon. This is because the decomposition or reverse reaction of the chlorinated saturated hydrocarbon which is the product of the chlorination reaction is promoted by the existence of iron. In the present invention, there is another advantage that iron is rarely contained in the product of the second reaction because the second reaction is preferably carried out in a gas phase.

The third reaction in the present invention may be carried out in a gas phase without condensing the unsaturated compound represented by the above general formula (2) or in a liquid phase by condensing the unsaturated compound.

When the third reaction is carried out in a gas phase in the present invention, it may be carried out in either a circulation or batch system. However, the circulation system is preferred from the viewpoint of reaction efficiency because a high degree of reaction conversion can be achieved in a short reaction time in the process of the present invention.

To carry out the third reaction in a gas phase in the process of the present invention, it can be carried out by heating a mixed gas of the exhaust gas of the second reaction and a chlorine gas at a predetermined temperature for a predetermined time. The amount of the chlorine gas is preferably 0.9 to 2.0 moles, more preferably 1.0 to 1.5 moles based on 1 mole of the dehydrochlorinated product (unsaturated compound represented by the above general formula (2)) contained in the reaction mixture of the second reaction. When this value is smaller than 0.9 mole, the degree of reaction conversion of the third reaction may be impaired and when the value is larger than 2.0 moles, the amount of the by-product may increase disadvantageously.

The reaction temperature of the chlorination reaction in the gas phase is preferably set to a range from the boiling point of the unsaturated compound represented by the above formula (2) to 300° C., more preferably from the boiling point to 280° C. in order to maintain the gas phase and suppress the production of the by-product. The reaction time is preferably 1 to 60 seconds, more preferably 1 to 40 seconds.

When the third reaction in the present invention is carried out in a liquid phase, the reaction temperature is not particularly limited as long as it falls within a temperature range at which the unsaturated compound represented by the above general formula (2) used as a feedstock does not evaporate but preferably 120° C. or lower in order to reduce the amount of the by-product. The amount of supplied chlorine is preferably 0.9 to 2.0 moles based on 1 mole of the unsaturated compound represented by the above general formula (2) in order to raise the degree of conversion and selectivity. The reaction time when the third reaction is carried out in a liquid phase is preferably 1 to 10 hours. To promote the liquid-phase reaction, it is preferred to blow chlorine as microscopic bubbles or apply ultraviolet light.

The exhaust gas or exhaust liquid of the third reaction obtained as described above is a crude product which contains the saturated compound represented by the above general formula (3) of interest in a high concentration. This crude product is purified by a known method as required to obtain a product. As the purification method which is carried out optionally may be used distillation purification. When distillation is carried out, to prevent the thermal decomposition of the compound represented by the above general formula (3), distillation is preferably carried out after a phenol derivative such as p-methoxyphenol, o-t-butylphenyl, eugenol or o-allylphenol, particularly a phenol derivative having an allyl group is added to the crude product.

When a mixture of the unsaturated compound represented by the above formula (2) and hydrogen chloride is subjected to the third reaction to be chlorinated without separating hydrogen chloride by-produced from the exhaust gas obtained by the second reaction, the crude product obtained by the third reaction contains hydrogen chloride and may contain unreacted chlorine. In this case, it is preferred that the following steps (A) to (C) should be made on the crude product to recover and recycle hydrogen chloride contained in the crude product.
(A) The step of separating hydrogen chloride (may contain unreacted chlorine) from the crude product obtained from the above third reaction,
(B) The step of oxidizing hydrogen chloride obtained from the above hydrogen chloride separation step, and
(C) The step of recycling chlorine obtained from the above oxidizing step as a chlorine source for the chlorination step The above hydrogen chloride separation step (A) can be carried out by a known method capable of separating hydrogen chloride, or hydrogen chloride and chlorine in some cases, from the crude product. An example of the method is a method in which the saturated compound represented by the above formula (3) contained in the crude product is condensed to separate hydrogen chloride, or hydrogen chloride and chlorine as a gas.

As the oxidation condition of hydrogen chloride in the above oxidation step (B), a known method is employed without restriction. An example of the method is a catalyst oxidation method. Stated more specifically, it is a method in which hydrogen chloride, or hydrogen chloride and chlorine are let pass through a titania catalyst layer supporting chromia or ruthenium in a gaseous state. The reaction temperature at this point is, for example, 200 to 450° C.

<production of high-purity 1,1,1,2,3-pentachloropropane>

A chlorinated hydrocarbon having high purity can be produced efficiently by carrying out a three-stage reaction or a reaction in any one of the stages in accordance with the process of the present invention as described above.

However, to produce high-purity 1,1,1,2,3-pentachloropropane quickly at a low cost by the above three-stage reaction, it is advantageous that the distillation purification of 1,1,1,3-tetrachloropropane should be carried out after the above first reaction and before the second reaction.

1,1,1,2,3-pentachlorpropane can be produced by a three-stage reaction consisting of a first reaction for obtaining 1,1,1,3-tetrachloropropane by adding carbon tetrachloride to ethylene as the unsaturated compound represented by the above general formula (0), a second reaction for obtaining at least one chlorinated saturated hydrocarbon selected from the group consisting of 3,3,3-trichloropropene and 1,1,3-trichloropropene by dehydrochlorinating the 1,1,1,3-tetrachloropropane, and a third reaction for obtaining 1,1,1,2,3-pentachloropropane by adding chlorine to the trichloropropene.

The reaction mixture obtained by the first reaction contains 1,1,1,3-tetrachloropropane as the main component and also carbon tetrachloride, hexachloroethane, tetrachloroethylene, 1,1,3-trichloropropene and 1,1,1,3,3-pentachloropropane as impurities. In the present invention, it is preferred that the content of hexachloroethane, tetrachloroethylene and 1,1,1,3,3-pentachloropropane out of the above impurities should be reduced as much as possible by purification after the first reaction. More specifically, the total weight of hexachloroethane, tetrachloroethylene and 1,1,1,3,3-pentachloropropane is reduced to preferably not more than 1 wt %, more preferably not more than 0.9 wt % based on the total weight of these and 1,1,1,3-tetrachloropropane. 1,1,1,2,3-pentachloropropane which is obtained as an object of interest after the third reaction contains substantially no impurities which are difficult to be separated by purifying the reaction mixture of the first reaction to the above extent after the first reaction and before the second reaction. Thereby, 1,1,1,2,3-pentachloropropane obtained by the process of the present invention can be used as a product directly, or 1,1,1,2,3-pentachloropropane having extremely high purity can be obtained by carrying out a simple purification method after that.

The inventors of the present invention have studied in detail the trends of impurities produced in each of the first, second and third reactions so as to attain the object of the present invention. As a result, they have found that hexachloroethane, tetrachloroethylene and 1,1,1,3,3-pentachloropropane which are produced as impurities in the first reaction cause a problem in purification after the third reaction.

That is, they have found that hexachloroethane remains unreacted even after the third reaction even when it undergoes the second reaction and the third reaction; tetrachloroethylene is converted into hexachloroethane in the chlorination reaction which is the third reaction although it does not react in the second reaction; and part of 1,1,1,3,3-pentachloropropane remains unreacted after the third reaction even when it undergoes the second reaction and the third reaction.

For explanation, the boiling points at normal pressure of an object of interest and impurities in the first reaction are shown in Table 1 and the boiling points at normal pressure of an object of interest and impurities in the third reaction are shown in Table 2.

TABLE 1

(after first reaction)

| | Compound | Boiling point (° C.) |
|---|---|---|
| Object of interest | 1,1,1,3-tetrachloropropane | 157 |
| Impurities | Hexachloroethane | 184 |
| | Tetrachloroethylene | 121 |
| | 1,1,1,3,3-pentachloropropane | 178 |

TABLE 2

(after third reaction)

| | Compound | Boiling point (° C.) |
|---|---|---|
| Object of interest | 1,1,1,2,3-pentachloropropane | 178 |
| Impurities | Hexachloroethane | 184 |
| | 1,1,1,3,3-pentachloropropane | 178 |

When purification is carried out by distillation, as understood from the above tables, there is an extremely small difference or no difference in boiling point between the object of interest and impurities after the third reaction (Table 2). Therefore, there is limitation to the purity of the object of interest obtained even when a very high-precision distillation apparatus is used. In contrast to this, after the first reaction, the difference in boiling point between the object of interest and impurities is large (Table 1) and therefore, the object of purification can be attained by a simple distillation apparatus.

When hexachloroethane, tetrachloroethylene and 1,1,1,3,3-pentachloropropane out of impurities are removed after the first reaction, hexachloroethane and 1,1,1,3,3-pentachloropropane cannot be existent in the reaction mixture after the third reaction. Therefore, when purification is carried out after the first reaction, the object of interest can be obtained without purification after the third reaction, or the object of interest having extremely high purity can be obtained by simple purification.

Attempts to produce high-purity pentachloropropane based on this idea have been unknown until now.

When distillation purification is carried out after the first reaction, as the distillation column in use, any distillation column which is known in the industry and used to distill a liquid substance at normal temperature and normal pressure may be used without restriction, and a plate column and a packed column are preferred. The number of stages of the plate column or the number of stages of the packed column calculated in terms of the plate column is preferably 2 to 20.

One distillation column or several distillation columns may be used. Out of these, use of several distillation columns is preferred because the removal efficiency of iron chloride dissolved in the reaction mixture becomes high.

As the above plate column may be used a crossflow tray or a shower tray. Examples of the crossflow tray include a porous plate tray, a bubble cap tray, a valve tray and a turbo grid tray; and examples of the shower tray include a turbo grid tray and a ripple tray. Out of these, a crossflow tray is preferred.

As the above packed column, a distillation column packed with a regular filler or an irregular filler may be used. Examples of the above irregular filler include a Raschig ring, Berl Saddle, Mcmahon, Nutter ring, Pall ring, Kascade mini ring and Heli pack. Out of these, use of a distillation column packed with a regular filler or a Kascade mini ring is preferred because the distillation efficiency can be increased.

The distillation temperature is preferably 60 to 140° C., more preferably 80 to 130° C. because it can suppress the decomposition of 1,1,1,3-tetrachloropropane and it is easy to control the distillation pressure. The distillation pressure is preferably set to a pressure capable of maintaining distillation operation at the above preferred temperature, for example, 1 to 20 kPa.

The reaction mixture of the first reaction (crude 1,1,1,3-tetrachloropropane, to be referred to as "crude TCP" hereinafter) is introduced into the distillation column from an appropriate position in a lower part of the distillation column, preferably from an intermediate stage. The heavy portion of the crude TCP is let fall from the introduction position and removed as a bottoms product. Meanwhile, it is preferred that the object of interest and acid matter contained in crude TCP should rise in the distillation column and the object of interest should be extracted as a column-side stream in the distillation column when the total content of impurities reaches a desired level. The expression "extracted as a column-side stream" means that a purified product is extracted from a liquid phase in at least a first stage right below the topmost stage of the distillation column, preferably a third to tenth stage from the topmost stage in which impurities are removed completely.

Since the acid matter is condensed in stages above the above extraction stage, it is preferred that an effluent from the top of the column should be separated into a condensate liquid and a noncondensate gas through a condenser, the noncondensate gas (containing acid matter in a high concentration) should be extracted and removed, and all or part of the condensate liquid should be refluxed into a stage above the stage for extracting the purified product. When the amount of the condensate liquid extracted is defined as the amount of a distillate and the reflux liquid is defined as the amount of the reflux liquid, the reflux ratio defined as (amount of reflux liquid)/(amount of distillate) is preferably 0.1 to 50, more preferably 1 to 40.

Further, it is also preferred that an inert gas should be introduced from a stage below the crude TCP introduction stage of the distillation column to promote the stripping effect of the acid matter contained in the liquid in the column. Examples of the inert gas used herein include nitrogen and helium. The amount of the inert gas introduced is preferably $1 \times 10^{-5}$ to $1 \times 10^{-3}$, more preferably $1 \times 10^{-5}$ to $1 \times 10^{-4}$ as the volume ratio to the total volume of the gas rising in the column.

The purified 1,1,1,3-tetrachloropropane (to be referred to as "purified TCP" hereinafter) obtained as described above does not substantially contain hexachloroethane, tetrachloroethylene and 1,1,1,3,3-pentachloropropane as impurities and therefore, 1,1,1,2,3-pentachloropropane which is obtained through the second reaction and the third reaction from the purified TCP does not contain hexachloroethane and 1,1,1,3,3-pentachloropropane as impurities. Consequently, 1,1,1,2,3-pentachloropropane after the third reaction can be used as a product directly, or a very high-purity product can be obtained by carrying out simple purification on this.

The simple purification which is carried out herein is, for example, distillation purification or a treatment with a deoxidizing agent.

Although distillation purification may be carried out in accordance with what has been described above as distillation purification which is preferably carried out after the above first reaction, since 1,1,1,2,3-pentachloropropane obtained by the process of the present invention does not contain impurities having a boiling point close to that of 1,1,1,2,3-pentachloropropane, the number of stages of the distillation column used for purification or the number of equivalent stages should be 2 to 20. This distillation is preferably carried out after the above phenol derivative, particularly a phenol derivative having an allyl group is added to crude 1,1,1,2,3-pentachloropropane.

The above treatment with a deoxidizing agent can be carried out by bringing 1,1,1,2,3-pentachloropropane into contact with a suitable deoxidizing agent. The deoxidizing agent used herein is selected from silica, alumina and silicate.

Examples of the above silica include amorphous silica, crystalline silica and silica hydrates such as silica gel and diatomaceous earth.

Examples of the above alumina include amorphous alumina, crystalline alumina and alumina hydrates.

The above silicate is not limited to a particular kind as long as it is a salt of silicon dioxide and a metal oxide. Examples of the silicate include alkali silicates such as sodium silicate; alkali earth metal silicates such as calcium silicate and magnesium silicate and aluminum silicate such as silica alumina gel. Minerals containing the above silicate include zeolite, synthetic zeolite, kaolinite, activated earth, halloysite, montmorillonite, allophane and bentonite.

A commercially available product such as Secard KW (of Shinagawa Chemicals Co., Ltd.) may be used as the above deoxidizing agent.

As for the shape of the deoxidizing agent, powdery, granular and particulate oxidizing agents may be used without restriction. The particle diameter of the deoxidizing agent is preferably small from the viewpoint of contact efficiency, and the average particle diameter of the deoxidizing agent is preferably not more than 9 mm, more preferably 0.3 to 5 mm.

The space velocity when 1,1,1,2,3-pentachloropropane is brought into contact with the deoxidizing agent is preferably 0.001 to 20 hr$^{-1}$, more preferably 0.005 to 10 hr$^{-1}$. The contact temperature is preferably 5 to 80° C., more preferably 10 to 70° C.

EXAMPLES

The following examples are provided for the purpose of further illustrating the present invention but are in no way to be taken as limiting.
<Examples of Three-Stage Reaction>

Example 1-1

(1) First Reaction
769 g of carbon tetrachloride, 4.5 g of triethyl phosphate and 14 g of iron powders (reduced iron of Wako Pure Chemical Industries, Ltd.) were fed to an SUS autoclave equipped with a stirrer, the temperature was set to 110° C., and ethylene was introduced into the autoclave so that a reaction pressure of 0.4 MPaG was maintained to start a reaction. After 6 hours, the autoclave was cooled, and the reaction solution after the reaction was collected and analyzed by gas chromatography to obtain its degree of conversion and selectivity. As a result, the degree of conversion was 80% based on carbon tetrachloride, and the selectivity toward 1,1,1,3-tetrachloropropane was 90%.
(2) Second Reaction (Dehydrochlorination Step)
1,1,1,3-tetrachloropropane formed in the above step was gasified by a preheater at 200° C., the flow rate was adjusted to ensure that the residence time became 2.5 seconds based on the flow rate of the gas at the inlet, and the gas was introduced into a reaction tube (made of SUS316, inner diameter of 4.35 mm, length of 300 mm) heated at 500° C. by an electric furnace to carry out a thermal decomposition reaction in a gas phase at normal pressure.
At this point, part of the formed gas obtained by the above second reaction was cooled to 0° C. to be liquefied and analyzed by gas chromatography so as to obtain its degree of conversion and selectivity. As a result, the degree of conversion was 99.7% and the selectivity toward 1,1,3-trichloropropene was 99.0%.
(3) Third Reaction (Chlorination Step)
The gas formed by the above second reaction was cooled to 150° C. and supplied into the chlorination step directly (without removing hydrogen chloride by-produced by the second reaction) to carry out chlorination in a gas phase under the following conditions.
A mixed gas prepared by introducing a chlorine gas into the supply line of the above formed gas (1,1,3-trichloropropene:chlorine=100:110 (molar ratio)) was let pass through a reaction tube having an inner diameter of 4.35 mm and a length of 300 mm to carryout a chlorination reaction for a residence time of 1.24 seconds, crude chloropropane obtained from the outlet of the reaction tube was then cooled to 0° C. to be liquefied so as to remove hydrogen chloride and unreacted chlorine, and the obtained product was purified by distillation to obtain 1,1,1,2,3-pentachloropropane of interest.
Part of the above liquefied crude chloropropane was extracted and analyzed by gas chromatography to obtain its degree of conversion and selectivity. As a result, the degree of conversion was 99% based on 1,1,3-trichloropropene, and the selectivity toward 1,1,1,2,3-pentachloropropane was 95%.

Example 1-2

(1) First Reaction
769 g of carbon tetrachloride, 4.5 g of triethyl phosphate and 14 g of iron powders (reduced iron of Wako Pure Chemical Industries, Ltd.) were fed to an SUS autoclave equipped with a stirrer, the temperature was set to 110° C., and vinyl chloride was introduced into the autoclave to ensure that a reaction pressure of 0.4 MPaG was maintained so as to start a reaction. After 6 hours, the autoclave was cooled, and the reaction solution after the reaction was collected and analyzed by gas chromatography to obtain its degree of conversion and selectivity. As a result, the degree of conversion was 81% based on vinyl chloride, and the selectivity toward 1,1,1,3,3-pentachloropropane was 91%.
(2) Second Reaction (Dehydrochlorination Step)
1,1,1,3,3-pentachloropropane formed in the above step was gasified by a preheater at 200° C., the flow rate was adjusted to ensure that the residence time became 2.5 seconds based on the flow rate of the gas at the inlet, and the gas was introduced into a reaction tube (made of SUS316, inner diameter of 4.35 mm, length of 300 mm) heated at 500° C. by an electric furnace to carry out a thermal decomposition reaction in a gas phase at normal pressure.
At this point, part of the formed gas obtained by the above second reaction was cooled to 0° C. to be liquefied and analyzed by gas chromatography so as to obtain its degree of conversion and selectivity. As a result, the degree of conversion was 99.1% and the selectivity toward 1,1,3,3-tetrachloropropene was 98.0%.
(3) Third Reaction (Chlorination Step)
The gas formed by the above second reaction was cooled to 180° C. and supplied into the chlorination step directly (without removing hydrogen chloride by-produced by the second reaction) to carry out chlorination in a gas phase under the following conditions.
A mixed gas prepared by introducing a chlorine gas into the supply line of the above formed gas (1,1,3,3-tetrachloropropene:chlorine=100:110 (molar ratio)) was let pass through a reaction tube having an inner diameter of 4.35 mm and a length of 300 mm to carry out a chlorination reaction for a residence time of 1.24 seconds, crude chloropropane obtained from the outlet of the reaction tube was cooled to 0° C. to be liquefied so as to remove hydrogen chloride and unreacted chlorine, and the obtained product was purified by distillation to obtain 1,1,1,2,3,3-hexachloropropane of interest.
Part of the above liquefied crude chloropropane was extracted and analyzed by gas chromatography to obtain its degree of conversion and selectivity. As a result, the degree of conversion was 99% based on 1,1,3,3-tetrachloropropane, and the selectivity toward 1,1,1,2,3,3-hexachloropropane was 90%.

Example 1-3

1,1,1,2,3-pentachloropropane was obtained in the same manner as in Example 1-1 except that the third reaction (chlorination step) was carried out as follows.
That is, trichloropropene formed by the second reaction (dehydrochlorination step) was liquefied to separate hydrogen chloride and then supplied into the third reaction so as to carry out a chlorination reaction at 80° C. while chlorine was supplied at a rate of 360 NmL/min (1,1,3-trichloropropene:chlorine=100:120 (molar ratio)). The supply rate of chlorine is a value in a standard state (SATP).
270 minutes after the start of the reaction, the reaction solution was analyzed by gas chromatography to obtain its degree of conversion and selectivity. As a result, the degree of conversion was 99% based on 1,1,3-trichloropropene, and the selectivity toward 1,1,1,2,3-pentachloropropane was 96%.
For the consideration of the effect of the three-stage reaction in the process of the present invention, please refer to the results of Examples 4-3, 4-4 and 4-6 which will be described hereinunder.

<Examples in which a Phosphate is Further Added in the First Reaction>

An addition reaction between ethylene and carbon tetrachloride was tested through a liquid-phase batch reaction under the circulation of a gas phase in the following Comparative Examples, Examples and Reference Examples.

As the reactor was used an SUS autoclave (inner volume of 1,500 mL) having a stirrer, an ethylene gas introduction port, a gas exhaust port and a phosphate further addition port. Ethylene was introduced into the gas phase through the above gas introduction port. During the reaction, the consumption speed of ethylene was monitored continuously from the difference between the amount of ethylene introduced from the gas introduction port and the amount of ethylene discharged from the gas exhaust port. During the reaction, the reaction pressure was controlled to 0.4 MPaG±0.02 MPa (5%).

The reaction mixture after the end of the reaction was analyzed by gas chromatography to obtain its degree of reaction conversion based on carbon tetrachloride in use, and the selectivity toward 1,1,1,3-tetrachloropropane as a product of interest.

The unit of the consumption speed of ethylene below is a value calculated in a standard state (SATP).

Comparative Example 2-1

1,560 g of carbon tetrachloride, 12 g of triethyl phosphate and 4 g of pure iron powders for chemical reactions (K-100T of JFE Steel Corporation) were fed to an autoclave, the temperature was set to 110° C., and ethylene was introduced to ensure that the reaction pressure became 0.4 MPaG so as to start an addition reaction.

After a little while from the start of the introduction of ethylene, the consumption of ethylene sharply rose. The average consumption speed of ethylene for 60 minutes from the start of the introduction of ethylene was 1,000 NmL/min, and the consumption speed of ethylene fell below 400 NmL/min 60 minutes after the start of the introduction of ethylene.

Six hours after the start of the introduction of ethylene, the autoclave was cooled, and the reaction mixture after the end of the reaction was collected and analyzed by gas chromatography. The degree of reaction conversion was 27% based on carbon tetrachloride in use, and the selectivity toward 1,1,1,3-tetrachloropropane was 86%.

Example 2-1

1,560 g of carbon tetrachloride, 8 g of triethyl phosphate and 4 g of pure iron powders for chemical reactions were fed to an autoclave, the temperature was set to 110° C., and ethylene was introduced to ensure that the reaction pressure became 0.4 MPaG so as to start an addition reaction.

After a little while from the start of the introduction of ethylene, the consumption of ethylene sharply rose. The average consumption speed of ethylene for 60 minutes from the start of the introduction of ethylene was 950 NmL/min. Since the consumption speed of ethylene fell below 400 NmL/min 60 minutes after the start of the introduction of ethylene, 4 g of triethyl phosphate was further added once.

Six hours after the start of the introduction of ethylene, the autoclave was cooled, and the reaction mixture after the end of the reaction was collected and analyzed by gas chromatography. The degree of reaction conversion was 85% based on carbon tetrachloride in use, and the selectivity toward 1,1,1,3-tetrachloropropane was 90%.

Example 2-2

1,560 g of carbon tetrachloride, 8 g of triethyl phosphate and 4 g of pure iron powders for chemical reactions were fed to an autoclave, the temperature was set to 110° C., and ethylene was introduced to ensure that the reaction pressure became 0.4 MPaG so as to start an addition reaction.

After a little while from the start of the introduction of ethylene, the consumption of ethylene sharply rose. The average consumption speed of ethylene for 60 minutes from the start of the introduction of ethylene was 950 NmL/min. 60 minutes after the start of the introduction of ethylene, the consumption speed of ethylene fell below 400 NmL/min. Then, triethyl phosphate was further added continuously for 250 minutes at a rate of 0.016 g/min 60 minutes after the start of the introduction of ethylene (the total amount of triethyl phosphate further added was 4 g).

Six hours after the start of the introduction of ethylene, the autoclave was cooled, and the reaction mixture after the end of the reaction was collected and analyzed by gas chromatography. The degree of reaction conversion was 93% based on carbon tetrachloride in use, and the selectivity toward 1,1,1,3-tetrachloropropane was 90%.

Reference Example 2-1

1,560 g of carbon tetrachloride, 12 g of triethyl phosphate and 60 g of pure iron powders for chemical reactions were fed to an autoclave, the temperature was set to 110° C., and ethylene was introduced to ensure that the reaction pressure became 0.4 MPaG so as to start an addition reaction.

Six hours after the start of the introduction of ethylene, the autoclave was cooled, and the reaction mixture after the end of the reaction was collected and analyzed by gas chromatography. The degree of reaction conversion was 85% based on carbon tetrachloride in use, and the selectivity toward 1,1,1,3-tetrachloropropane was 86%.

Reference Example 2-2

1,560 g of carbon tetrachloride, 14 g of dibutyl phosphate and 60 g of pure iron powders for chemical reactions were fed to an autoclave, the temperature was set to 100° C., and ethylene was introduced to ensure that the reaction pressure became 0.4 MPaG so as to start an addition reaction.

Six hours after the start of the introduction of ethylene, the autoclave was cooled, and the reaction mixture after the end of the reaction was collected and analyzed by gas chromatography. The degree of reaction conversion was 21% based on carbon tetrachloride in use, and the selectivity toward 1,1,1,3-tetrachloropropane was 85%.

It is understood from the above results that when iron and a phosphate are used in the same amounts, the process of the present invention (Examples 2-1 and 2-2) in which the whole amount of iron and part of the phosphate are added before the start of the reaction and the remaining phosphate is added during the proceeding of the addition reaction is superior to the prior art process in which the whole amounts of these are added at the same time before the start of the reaction (Comparative Example 2-1) in both the degree of reaction conversion and selectivity.

<Examples of Three-Stage Reaction in which the Distillation Purification of Product is Carried Out after First Reaction and Before Second Reaction>

Example 3-1

(1) First Reaction 1,560 g of carbon tetrachloride, 8 g of triethyl phosphate and 4 g of pure iron powders for chemical reactions were fed to an autoclave, the temperature was set to 110° C., and ethylene was introduced into the autoclave to ensure that the reaction pressure became 0.4 MPaG so as to start the first reaction (addition reaction). One hour after the start of the introduction of ethylene, 4 g of triethyl phosphate was further added.

Six hours after the start of the introduction of ethylene, the autoclave was cooled, and the reaction mixture after the end of the reaction was collected and analyzed by gas chromatography. The degree of conversion of carbon tetrachloride in use was 85% and the selectivity toward 1,1,1,3-tetrachloropropane was 90%.

(2) Purification after First Reaction

The two-stage distillation purification of the reaction mixture obtained by the above first reaction was carried out as follows.

As first time of distillation, batch distillation was carried out at a distillation pressure of 10 kPa and a distillation temperature of 95° C. without refluxing in a distillation column having a column diameter of 30 mm and filled with the glass packing of Shibata Scientific Technology Ltd. to a height of 500 mm. The purity of 1,1,1,3-tetrachloropropane out of purified fractions obtained herein was 98.5%.

As second time of distillation, the batch distillation of the purified fractions obtained as described above was carried out at a reflux ratio of 3, a distillation pressure of 10 kPa and a distillation temperature of 95° C. in a distillation column having a column diameter of 30 mm and filled with the glass packing of Shibata Scientific Technology Ltd. to a height of 1,000 mm. At this point, the purity of purified 1,1,1,3-tetrachloropropane which was a distillate obtained by removing 4 wt % of a low-boiling fraction and 6 wt % of a bottom high-boiling residue was almost 100%.

(3) Second Reaction

The second reaction (dehydrochlorination reaction) was carried out at a residence time of 2.5 seconds and a reaction temperature of 500° C. by using the purified 1,1,1,3-tetrachloropropane obtained above. The degree of reaction conversion by this dehydrochlorination reaction was 99.7%, and the selectivity toward 1,1,3-trichloropropene of interest was 99.0%. The above degree of conversion and selectivity were calculated based on 1,1,1,3-tetrachloropropane.

(4) Third Reaction

In the third reaction (chlorination reaction), the exhaust gas of the above second reaction was cooled to 150° C. and mixed with a chlorine gas whose flow rate was adjusted, and the resulting mixed gas was supplied into a reactor to carry out a chlorination reaction at a residence time of 1.24 seconds so as to obtain crude 1,1,1,2,3-pentachloropropane. The flow rate of the chlorine gas was set to 1.1 m$^3$ (0° C., 98 kPa) based on 1 m$^3$ (0° C., 98 kPa) of the exhaust gas of the second reaction. The degree of reaction conversion in the chlorination reaction was 99.0%, and the selectivity toward 1,1,1,2,3-pentachloropropane of interest was 95.0%. The above degree of conversion and selectivity were calculated based on 1,1,3-trichloropropene.

(5) Purification after Third Reaction

The batch distillation of crude 1,1,1,2,3-pentachloropropane obtained by the above third reaction was carried out at a reflux ratio of 3, a distillation pressure of 10 kPa and a distillation temperature of 135° C. in a distillation column having a column diameter of 30 mm and filled with the glass packing of Shibata Scientific Technology Ltd. to a height of 1,000 mm. The purity of the purified 1,1,1,2,3-pentachloropropane which was a distillate obtained by removing 3 wt % of a low-boiling fraction and 7 wt % of a bottom high-boiling residue was almost 100%. The acid content at this point was 210 ppm by weight Separately, when a distillate was sampled from a portion 100 mm below the top of the distillation column (corresponding to 0.2 stage below the top of the column), the purity of the purified 1,1,1,2,3-pentachloropropane was almost 100%, and the acid content was 40 ppm by weight.

(6) Trend of Each Component

The trend of each component in each reaction and each purification is shown in Table 3.

Example 3-2

An effluent of purified 1,1,1,2,3-pentachloropropane was obtained in the same manner as in Example 1 except that a column filled with Secard KW (trade name, manufactured by Shinagawa Chemicals Co., Ltd.) was installed at the distillate port (top of the column) of the distillation column for crude 1,1,1,2,3-pentachloropropane in the above Example 3-1. The space velocity in contact between 1,1,1,2,3-pentachloropropane fraction and the Secard KW was 1 hr$^{-1}$.

The trend of each component in this Example was the same as in Example 3-1. The acid content of the above purified 1,1,1,2,3-pentachloropropane was 20 ppm by weight.

Example 3-3

An effluent of purified 1,1,1,2,3-pentachloropropane was obtained from the distillate port (top of the column) in the same manner as in Example 1 except that the distillation pressure of the distillation column used for purification after the third reaction was set to 5 kPa and the distillation temperature was set to 110° C. in the above Example 3-1.

The trend of each component in this Example was the same as in Example 3-1. The acid content of the above purified 1,1,1,2,3-pentachloropropane was 90 ppm by weight.

Comparative Example 3-1

An effluent of purified 1,1,1,2,3-pentachloropropane was obtained from the distillate port at the top of the column in the same manner as in Example 1 except that distillation purification was not carried out after the first reaction in the above Example 1. The acid content of the above purified 1,1,1,2,3-pentachloropropane was 210 ppm by weight.

The trend of each component in this Comparative Example is shown in Table 4.

TABLE 3

(Examples 3-1 to 3-3)

| | Composition ratio (wt %) | | | | |
| | | After distillation after first reaction | | | After |
| Component | After first reaction | After first time of distillation | After second time of distillation | After third reaction | distillation after third reaction |
| --- | --- | --- | --- | --- | --- |
| Carbon tetrachloride | 12.8 | 0.2 | 0.0 | 0.0 | 0.0 |
| Tetrachloroethylene | 0.3 | 0.4 | 0.0 | 0.0 | 0.0 |
| 1,1,3-trichloropropane | 0.2 | 0.2 | 0.0 | 0.7 | 0.0 |

TABLE 3-continued (Examples 3-1 to 3-3)

| | Composition ratio (wt %) | | | | |
|---|---|---|---|---|---|
| | | After distillation after first reaction | | | After |
| Component | After first reaction | After first time of distillation | After second time of distillation | After third reaction | distillation after third reaction |
| 1,1,1,3-tetrachloropropane | 77.5 | 98.5 | 100.0 | 0.3 | 0.0 |
| Impurity 1 | 0.0 | 0.0 | 0.0 | 0.8 | 0.0 |
| Hexachloroethane | 0.3 | 0.4 | 0.0 | 0.0 | 0.0 |
| 1,1,1,3,3-pentachloropropane | 0.2 | 0.3 | 0.0 | 0.0 | 0.0 |
| 1,1,1,2,3-pentachloropropane | 0.0 | 0.0 | 0.0 | 93.3 | 100.0 |
| Impurity 2 | 0.0 | 0.0 | 0.0 | 4.9 | 0.0 |
| Impurity 3 | 8.7 | 0.0 | 0.0 | 0.0 | 0.0 |
| Total | 100.0 | 100.0 | 100.0 | 100.0 | 100.0 |

TABLE 4

(Comparative Examples 3-1)

| | Composition ratio (wt %) | | |
|---|---|---|---|
| Component | After first reaction | After third reaction | After distillation after third reaction |
| Carbon tetrachloride | 12.8 | 0.2 | 0.0 |
| Tetrachloroethylene | 0.3 | 0.3 | 0.0 |
| 1,1,3-trichloropropane | 0.2 | 0.6 | 0.0 |
| 1,1,1,3-tetrachloropropane | 77.5 | 0.2 | 0.0 |
| Impurity 1 | 0.0 | 0.8 | 0.0 |
| Hexachloroethane | 0.3 | 0.4 | 0.4 |
| 1,1,1,3,3-pentachloropropane | 0.2 | 0.3 | 0.3 |
| 1,1,1,2,3-pentachloropropane | 0.0 | 92.3 | 99.3 |
| Impurity 2 | 0.0 | 4.9 | 0.0 |
| Impurity 3 | 8.7 | 0.0 | 0.0 |
| Total | 100.0 | 100.0 | 100.0 |

The boiling points of impurities 1 to 3 in Table 3 and Table 4 were estimated at 165° C., 200° C. and 210° C., respectively.

<Examples in which Second Reaction is Carried Out by Thermal Decomposition>

Example 4-1

1,1,1,3-tetrachloropropane which was gasified by a preheater at 200° C. was introduced into a reaction tube (made of SUS 316, inner diameter of 4.35 mm, length of 300 mm) heated at 500° C. by an electric furnace in a gaseous state by controlling its flow rate to ensure that its residence time became 2.5 seconds based on the flow rate of the gas at the inlet so as to carry out a thermal decomposition reaction in a gas phase at normal pressure.

The gas at the exit was cooled to 0° C. to be liquefied and analyzed by gas chromatography so as to obtain its degree of conversion and selectivity toward 1,1,3-trichloropropene.

The results are shown in Table 5.

Example 4-2

Thermal decomposition was carried out in the same manner as in Example 4-1 except that the temperature of the reaction tube was changed to 450° C.

The analytical results of the degree of conversion and selectivity are shown in Table 5.

Example 4-3

Thermal decomposition was carried out in the same manner as in Example 4-1 except that the temperature of the reaction tube was changed to 550° C.

The analytical results of the degree of conversion and selectivity are shown in Table 5.

Example 4-4

Thermal decomposition was carried out in the same manner as in Example 4-1 except that the residence time was changed to 1.25 seconds.

The analytical results of the degree of conversion and selectivity are shown in Table 5.

Example 4-5

Thermal decomposition was carried out in the same manner as in Example 4-1 except that 1,1,1,2-tetrachloropropane was used as a feedstock in place of 1,1,1,3-tetrachloropropane and the temperature of the reaction tube was changed to 450° C.

The analytical results of the degree of conversion of 1,1,1,2-tetrachloropropane and the selectivity toward 1,1,2-trichloropropene are shown in Table 5.

Example 4-6

Thermal decomposition was carried out in the same manner as in Example 4-1 except that 1,1,1,3-tetrachloropropane as a feedstock was diluted with a nitrogen gas to a concentration of 75% and supplied into the reaction tube.

The analytical results of the degree of conversion and selectivity are shown in Table 5.

Example 4-7

1,1,1,3-tetrachloropropane which was gasified by a preheater at 200° C. was introduced into a reaction tube (made of SUS316, inner diameter of 7.3 mm, length of 600 mm) heated at 450° C. by an electric furnace in a gaseous state by controlling its flow rate to ensure that its residence time became 9.0 seconds based on the flow rate of the gas at the inlet so as to carry out a thermal decomposition reaction in a gas phase at normal pressure.

The analytical results of the degree of conversion and selectivity are shown in Table 5.

TABLE 5

(Examples 4-1 to 4-7)

| | Decomposition temperature (° C.) | Residence time (seconds) | Degree of conversion (%) | Selectivity (%) |
|---|---|---|---|---|
| Example 4-1 | 500 | 2.5 | 99.7 | 99.0 |
| Example 4-2 | 450 | 2.5 | 85.4 | 99.8 |
| Example 4-3 | 550 | 2.5 | 99.7 | 92.9 |
| Example 4-4 | 500 | 1.25 | 88.7 | 99.6 |
| Example 4-5 | 450 | 2.5 | 99.5 | 95.3 |
| Example 4-6 | 500 | 2.5 | 99.8 | 99.5 |
| Example 4-7 | 450 | 9.0 | 99.8 | 99.3 |

EFFECT OF THE INVENTION

According to the present invention, there is provided a process which has the following advantages in each of three steps for the manufacture of a chlorinated hydrocarbon.

There are provided a process for carrying out an addition reaction efficiently at a stable reaction rate to obtain a product of interest having a high degree of conversion while the amount of a catalyst in use is reduced in a first reaction; a process for carrying out a dehydrochlorination reaction in which the production of a by-product to be disposed of is suppressed without using an expensive alkali source in a second reaction; and a process for carrying out a highly efficient chlorination reaction in a third reaction.

According to the present invention, a high-purity chlorinated hydrocarbon can be produced efficiently with simple operation.

The invention claimed is:

1. A process of making a chlorinated hydrocarbon by obtaining a saturated compound represented by the following general formula (1'), comprising:
an addition reaction step comprising adding carbon tetrachloride to an unsaturated compound represented by the following general formula (0) in a liquid-phase reaction system in the presence of an iron-phosphate catalyst, wherein:
the iron-phosphate catalyst is prepared in the reaction system by adding iron and a phosphate to the reaction system;
the whole amount of iron and part of the phosphate are added before the start of the reaction, and the remaining phosphate is added during the addition reaction step; and
an amount of the phosphate to be added before the start of the reaction is not less than 0.0005 mole based on 1 mole of carbon tetrachloride in use, and not more than 70% of a total amount of the phosphate,

  (0)

  (1')

wherein m is 1 or 2, and p is an integer of 0 to 2, with the proviso that m≧p.

2. The process according to claim 1, wherein the addition of the remaining phosphate is carried out only once or 2 to 10 times, and wherein the first addition of the remaining phosphate is carried out when the consumption speed of the unsaturated compound represented by the above general formula (0) becomes 5 to 50% of the average consumption speed for 60 minutes from the start of the reaction.

3. The process according to claim 1, wherein the addition of the remaining phosphate is carried out continuously, and wherein the addition of the remaining phosphate is started when the consumption speed of the unsaturated compound represented by the above general formula (0) becomes 5 to 50% of the average consumption speed for 60 minutes from the start of the reaction.

4. The process according to claim 1, wherein the total amount of the phosphate is 0.001 to 5 mole based on 1 mole of carbon tetrachloride in use.

5. The process according to claim 2, wherein the total amount of the phosphate is 0.001 to 5 mole based on 1 mole of carbon tetrachloride in use.

6. The process according to claim 3, wherein the total amount of the phosphate is 0.001 to 5 mole based on 1 mole of carbon tetrachloride in use.

7. The process according to claim 1, wherein the amount of the iron which is entirely added before the start of the reaction is 0.0001 to 1 mole based on 1 mole of carbon tetrachloride in use.

8. The process according to claim 2, wherein the amount of the iron which is entirely added before the start of the reaction is 0.0001 to 1 mole based on 1 mole of carbon tetrachloride in use.

9. The process according to claim 3, wherein the amount of the iron which is entirely added before the start of the reaction is 0.0001 to 1 mole based on 1 mole of carbon tetrachloride in use.

10. The process according to claim 4, wherein the total amount of the phosphate is 0.001 to 0.0065 mole based on 1 mole of carbon tetrachloride in use.

11. The process according to claim 5, wherein the total amount of the phosphate is 0.001 to 0.0065 mole based on 1 mole of carbon tetrachloride in use.

12. The process according to claim 6, wherein the total amount of the phosphate is 0.001 to 0.0065 mole based on 1 mole of carbon tetrachloride in use.

* * * * *